United States Patent [19]

Wenke

[11] Patent Number: 5,413,612
[45] Date of Patent: May 9, 1995

[54] COMPOSITION AND METHOD FOR DYEING HAIR WITH INDOLIC COMPOUNDS IN THE PRESENCE OF A CHLORITE OXIDANT

[75] Inventor: Gottfried Wenke, Woodridge, Conn.

[73] Assignee: Clairol Incorporated, New York, N.Y.

[21] Appl. No.: 13,441

[22] Filed: Feb. 4, 1993

Related U.S. Application Data

[63] Continuation-in-part of Ser. No. 875,874, Apr. 29, 1992, abandoned.

[51] Int. Cl.$^6$ ................................................. A61K 7/13
[52] U.S. Cl. .......................................... 8/423; 8/405; 8/406; 8/408; 8/409
[58] Field of Search ............... 8/412, 406, 407, 408, 8/410, 421, 429, 405, 409, 423; 424/70

[56] References Cited

U.S. PATENT DOCUMENTS

| | | | |
|---|---|---|---|
| 2,934,396 | 4/1960 | Charle et al. | 8/11 |
| 3,194,734 | 7/1965 | Seemuller et al. | 167/88 |
| 3,214,472 | 10/1965 | Charle et al. | 260/571 |
| 3,236,734 | 2/1966 | Charle et al. | 167/88 |
| 4,013,404 | 3/1977 | Parent et al. | 8/11 |
| 4,776,857 | 10/1988 | Carroll et al. | 8/406 |
| 5,011,500 | 4/1991 | Grollier et al. | 8/410 |
| 5,032,138 | 7/1991 | Wolfram et al. | 8/408 |
| 5,073,174 | 12/1991 | Vayssie et al. | 8/406 |
| 5,096,455 | 3/1992 | Grollier | 8/409 |
| 5,131,911 | 7/1992 | Lang et al. | 8/410 |
| 5,173,085 | 12/1992 | Brown et al. | 8/405 |

FOREIGN PATENT DOCUMENTS 0887579  1/1962  United Kingdom .

Primary Examiner—Christine Skane
Assistant Examiner—Caroline L. Dusheck
Attorney, Agent, or Firm—Charles J. Zeller

[57] ABSTRACT

Aqueous dye compositions containing sodium chlorite together with 5,6-dihydroxyindoline or 5,6-dihydroxyindole, its analogs, homologs or derivatives, methods of using the compositions to color hair and packages containing such compositions.

13 Claims, No Drawings

COMPOSITION AND METHOD FOR DYEING HAIR WITH INDOLIC COMPOUNDS IN THE PRESENCE OF A CHLORITE OXIDANT

RELATED APPLICATION

This application is a continuation in part of commonly owned application Ser. No. 07/875,874 filed Apr. 4, 1992, now abandoned.

FIELD OF THE INVENTION

This invention concerns methods and compositions for dyeing human hair.

BACKGROUND OF THE INVENTION

Modern hair dyeing methodology has developed from its initiation in the 1950s to the point where today it is the third largest product type in the hair care category, following shampoos and conditioners.

One widely employed method for dyeing hair is based upon the production of the natural pigment melanin. The exact structure of melanin it not known. It is a polymer produced from tyrosine by a series of metabolic reactions the exact course of which remains to be clarified. To take advantage of what has been elucidated with respect to the formation of melanin, it has become the practice of the art to utilize 5,6-dihydroxyindole (DHI) or 5,6-dihydroxyindole-2-carboxylic (DHICA) as the dyeing agent. These compounds have been clearly established as intermediates in the pathway leading to the production of melanin.

There are a number of problems associated with the use of DHI. It is difficult and expensive to synthesize and is extremely unstable in air. It rapidly decomposes in air to form other materials which are ineffective as hair colorants.

Diacetoxyindole (DAI) is used by the art in its attempts to avoid these problems with DHI. The practice has been to package DAI under mildly alkaline conditions in packages designed to protect the ingredients from air. Over the course of the time, between the initial packaging and the final use, the DAI is hydrolyzed to DHI. Since it is protected from air by the packaging, the DHI remains stable until it is ready for use.

It is known that use of DHI alone requires a long dyeout time. Therefore a variety of accelerators has been employed to hasten the dye formation. Oxidants, such as hydrogen peroxide, are the most widely employed of the various accelerators which have been proposed.

The use of oxidants has not been particularly successful with DHI, because oxidation takes place before the DHI penetrates the hair. Ideally, the DHI should penetrate the hair before oxidation takes place so that the pigment forms within the hair fiber. When the colorant forms in this manner, the color does not easily wash out. In contrast, if oxidation and melanin formation take place in the solution there is little or no dyeing effect. If oxidation takes place on the surface of the hair, the coloring is easily washed away during shampooing.

In attempts to avoid these problems, the art has adopted a two step process. DHI is applied first and allowed to penetrate into the hair. The oxidant is applied in a second step. This procedure is described, for example, in U.S. Pat. No. 2,934,396. Such procedures are lengthy and inconvenient.

It is one object of this invention to provide a one-step dyeing procedure, that is, a method, in which DHI and oxidant are applied to the hair simultaneously.

Dyeing with DHI is very attractive to many consumers, since its conversion to melanin is close to the natural pigmentation process. However, there are disadvantages. One such disadvantage is that, while natural hair color comes in an inexhaustible variety of shades, many oxidants which are used in combination with DHI dye the hair only to a gray or black color with little or no warmth. Extensive research efforts have been undertaken to find ways to modify the final color result after dyeing with DHI.

One way to obtain a brown tonality is through use of hydrogen peroxide. In this procedure, the hair is first dyed black through formation of melanin and then partially bleached to brown through destruction of part of the melanin. A clear disadvantage is the waste of DHI, which is supplied at the beginning. This is important, because DHI is an expensive raw material, and will control the price of the final product.

A second disadvantage is the fact that uneven and unpredictable results are often obtained due to the heterogeneity of living hair and the difference in its affinities for the dye, which vary from one person to another.

A third disadvantage is the likelihood of oxidative damage to the keratin of the hair as a result of the use of a product, containing peroxide—noticeable in a coarse feel of the hair. Moreover, hydrogen peroxide is normally used under alkaline conditions, with ammonia or an amine as the alkaline reagent. These alkaline reagents impart strong odors to the hair dyeing compositions and are unacceptable to many users.

A fourth disadvantage is that peroxide attacks and partly destroys the natural hair pigment. This weakens the hair and changes its feel and appearance.

For these reasons, many efforts have been undertaken in the art to avoid the problems connected with the use of hydrogen peroxide.

It is, therefore, another object of the invention to provide a method to dye hair to a dark brown shade without using hydrogen peroxide.

Comparison With Prior Art

As described above, U.S. Pat. No. 2,934,396 teaches that dyeing with DHI requires two steps.

U.S. Pat. No. 3,236,734 teaches dyeing with 1-(alkylamino)-2,4-dihydroxy benzene and an oxidant in one or two steps. Chlorites, but not sodium chlorite specifically, are mentioned among the oxidants said to be useful, but according to the teaching of this patent, all oxidants work equally well with the specified substrate, 1-(alkylamino)-2,4-dihydroxy benzene. This is clearly not the case, when DHI is used, as will be demonstrated later in the examples (Example 1).

It should be understood, that under the heading "peroxide", there might also be compounds, which produce peroxide after being dissolved in water; for example, perborate, percarbonate, urea peroxide and the like.

As will be shown in the examples, at a given concentration of DHI and with equal dyeing time, sodium chlorite gives the darkest coloration on hair, and provides the most economic use of the DHI.

U.S. Pat. No. 3,194,734 teaches the use of a variety of oxidizing agents with DHI or with 1-, 2- or 3- methyl substituted DHI derivatives in alkaline media in a one- or two-step process to color hair. Sodium chlorite is not mentioned in the patent.

As will be seen in the examples (Example 3), among all the oxidants, which are listed in the patent, only peroxide gives useful results in a one-step dyeing process with DHI. Moreover, in order to obtain dark dyeings at a relatively low concentration of DHI, the presence of a substantial amount of ammonia is required. As stated above, this causes unacceptable odor problems.

U.S. Pat. No. 5,032,138 teaches dyeing with standard oxidation dyes (primary intermediates and couplers) in combination with chlorite. Melanin precursors are not included in the patent.

U.S. Pat. No. 2,944,869 teaches dyeing of hair with o-diphenols and an oxidant, selected from ammonium and alkali metal iodates, periodates or persulfates. However, these oxidants, when used in a one-step treatment with DHI, give only weak colors on hair, since most of the DHI is oxidized and polymerized in solution, before it can penetrate the hair.

The art has long sought a suitable oxidizing agent which can be employed without the problems discussed above. More specifically, the art has sought dye compositions which will produce melanin in hair and give the hair a desirable color, with lasting wear qualities, in shorter periods of time, while avoiding the use of hydrogen peroxide and its resulting oxidative and bleaching damage to the hair.

SUMMARY OF THE INVENTION

Oxidative hair dyeing compositions and methods for their use have now been discovered which avoid many of the problems of prior art compositions. These novel compositions are characterized by the use of sodium chlorite as the oxidizing agent. The use of sodium chlorite, with 5,6-dihydroxyindoline, DHI or selected analogs, homologs or derivatives thereof, or with these compounds together with oxidizable primary intermediates and couplers, or together with DHICA or its lower alkyl esters, for example methyl to hexyl esters including straight chain and branched chain alkyl esters has not been specifically taught or suggested by any of the above citations nor, so far as the inventors are aware, by any other prior art.

DHI and DHI derivatives, analogs and homologs which may be employed in the practice of this invention include melanin forming compounds represented by the formula:

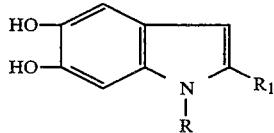

I wherein R represents hydrogen, alkyl, hydroxyalkyl, aminoalkyl, an alkyl group containing up to eight carbon atoms; aryl or substituted aryl containing up to three reaction inert substituents; $R_1$ represents hyrogen or alkyl containing up to six carbon atoms; and mixtures of said compounds. The compound 5,6-dihydroxyindoline is also useful in this invention because under the conditions employed, it is oxidized to dopaminochrome which rearranges to DHI. The DHI then converts to melanin in accordance with the invention.

The preferred N-substituted compounds of the present invention are those of structure I where the N-substituent, R, is hydrogen, alkyl, hydroxyalkyl, aminoalkyl, containing 1 to about 8 carbon atoms in the moiety or a substituted or unsubstituted aryl wherein aryl substituents are reaction inert substituents such as OH, $NH_2$, alkyl, alkoxyl, or $NO_2$. The most preferred compound is DHI.

For convenience, the invention will hereinafter be described principally with reference to DHI, but it should be remembered that the invention is applicable to all of the compounds within the scope of the above generic formula and their equivalents. The various compounds may be used alone or in numerous mixtures, including mixtures with other oxidative dyes or with DHICA or its lower alkyl esters, to achieve a variety of shades and tonal qualities with hair fibers.

It is most unexpected to find that this specific oxidizing agent will accelerate the formation of melanin, but not to such an extent that DHI is oxidized appreciably before it is distributed in the hair fiber.

It is equally surprising and unexpected to find that sodium chlorite imparts a dark brown color of natural appearance to the hair at relatively low concentrations of DHI and without the use of ammonia or other amines.

A further surprising aspect of the invention is the finding that DHICA and its lower alkyl esters or oxidizable primary intermediates and couplers can be employed in association with sodium chlorite and DHI to achieve a wider variety of tonalities in the treated hair.

There are many advantages to the compositions and methods of the invention. These include:

1. Melanin is formed in the hair, imparting a brown color of natural appearance with relatively low concentrations of DHI. These low concentrations are possible, because none of the melanin, which was already present in the fiber, or is formed during dyeing, is destroyed. This results is cost savings for the manufacturer as well as for the consumer.

2. Melanin is deposited in a predictable and reproducible way. Dyeing results are even and appealing.

3. The dyeing procedure is simple (one-step) and fast.

4. Sodium chlorite does not cause oxidative damage to human hair or to the natural hair pigment, as does hydrogen peroxide.

5. The wear quality of the colors produced in the dyed hair is appreciably enhanced i.e. the original dyed color is retained for a longer period of time.

6. The actual coloring of the hair can be performed at a pH which is at, or close to, neutrality.

7. The odor may be markedly reduced because ammonia or amines are omitted from the compositions.

DETAILED DESCRIPTION OF THE INVENTION

The compositions of this invention as applied to human hair, either living or in a wig or other artificial device with implanted human hair, comprise an aqueous vehicle which may contain a water miscible solvent, such as a lower alkanol, typically ethanol or isopropanol to aid solubility, together with DHI, or other compound(s) of the class defined above. Other compositions of the invention may contain DHI and/or a derivative, analog or homolog together with DHICA or lower alkyl ester, or a primary intermediate/coupler combination. Of course, if such combination is employed, it may contain more than one intermediate or coupler to achieve a variety of shades.

A typical aqueous composition of the invention as applied to the hair may contain from about 0.1% to 3%, preferably 0.3% to 1.5% DHI or DHI analog, homolog or derivative, and from about 0.1% to 5%, preferably 0.5% to 4% of sodium chlorite. It is generally preferred to employ lower concentrations of the oxidizing agent when the concentration of DHI utilized is at the low end of the range. The pH is normally from about 7 to 9, but some variation is acceptable.

All percent by weights defined in this disclosure and claims are percents by weight based on the total weight of the composition.

As stated above, the concentration of the DHI in the composition as applied to the hair is from about 0.1 to 3%. It was also noted above that DHI is rather unstable and subject to air oxidation. It is therefore normally packaged for commercial use in the form of DAI in a slightly alkaline solution, under conditions that substantially exclude air. On storage, under alkaline conditions, the DAI hydrolyzes to form DHI. The molecular weight of DHI is about 60% lower than the molecular weight of DAI. Accordingly, the concentration of DAI in the original package will be higher than the concentration of DHI in the package as ready for use. Of course, it is possible, if sufficient precautions are taken, to prepare an original package containing DHI.

If, in accordance with a second embodiment of this invention, the DHI and oxidant are utilized together with oxidizable primary intermediates and couplers (hereinafter sometimes called "reactants"), the amounts of reactants will be about the same as utilized in conventional oxidant compositions. The amounts which will be tinctorially effective will vary with the selected reactants, as is well known in the art. The skilled artisan will have no difficulty in selecting the reactants and the amounts to be employed. Generally each reactant will be present in an amount of from about 0.01 to 2%, preferably 0.01 to 0.5%.

If DHICA or a lower alkyl ester of DHICA is employed in a formulation of the invention, the amount employed will typically be from about 0.1 to 1%.

The oxidant will be separately formulated to mix with the other components just prior to use, as illustrated in the examples. Thus, a product of the invention may comprise a package containing two separate units of aqueous compositions, one containing the oxidant, the other containing DHI and, if employed, a primary intermediate and a coupler.

The term "package" is used in the widest possible sense. It includes retail packages such as might be sold to an individual consumer with both compositions in the same box or other container. It includes also separate compositions in large amounts, such as might be sold to a beauty salon, whether or not the separate compositions are sold in the same container and are intended to be used together.

The compositions of this invention are particularly adapted for co-dispensing from a compartmentalized package, such as the containers described in U.S. Pat. Nos. 3,241,722 and 4,103,772, the disclosures of which are incorporated herein by reference. In such co-dispensing packages, which have been employed previously with hydrogen peroxide dye systems, the reactants are normally sealed in one compartment of the container and the hydrogen peroxide in another, and the container is constructed with means for mixing the separate ingredients in the container so that the resulting composition exits the container after such mixing.

There are two procedures for mixing which are normally employed. One utilizes an aerosol package and valve adapted so that the compositions in the compartments mix as they pass through the valve. In the other, the partition between the compartments is frangible and the container is formed with a mechanism which permits the partition to be pierced, or otherwise broken, so that the compositions mix prior to dispensing. Depending upon the design of the container, the resulting mixed composition can be dispensed under aerosol pressure, by simple pouring or by any other convenient method.

When such co-dispensing containers are employed with hydrogen peroxide systems, there is always danger of premature mixing because of accidental leakage through the partition. As a result the dye forming reaction, which is intended to take place in the open air takes place in a closed container thereby generating volumes of oxygen which may result in explosive pressure. There is no such danger when the oxidative salts of this invention are employed since the dye forming reaction does not generate oxygen.

Any of the conventional oxidizable primary intermediates and coupling agents used with ordinary oxidant compositions for hair coloring can be employed in the compositions of this invention to achieve, together with the DHI, a wide variety of tints and hues.

Table 1 below lists some of the preferred primary intermediates and couplers for use in this invention.

TABLE 1

| Primary Intermediates: | p-phenylenediamine<br>p-aminophenol<br>o-aminophenol<br>N,N-bis(2-hydroxyethyl)p-phenylenediamine<br>2,5-diaminopyridine<br>p-toluenediamine |
|---|---|
| Couplers: | resorcinol<br>m-aminophenol<br>1-naphthol<br>5-amino-o-cresol<br>2-methylresorcinol<br>4,6-di(hydroxyethoxy)-meta-phenylenediamine<br>meta-phenylenediamine |

Well known conventional additives usually employed in oxidative hair coloring compositions such as thickeners, surface active agents, antioxidants and fragrances may be included in the compositions of the invention. Such compositions are preferably liquid solutions, but they may be in the form of emulsions, suspensions, lotions, or gels.

Surface active agents employed in the dyeing compositions of this invention can be amphoteric, anionic, nonionic or cationic. By way of examples of the various types of surface active agents, there can be mentioned: higher alkylbenzene sulfonates: alkylnaphthalensulfonates: sulfonated esters of alcohols and polybasic acids; taurates; fatty alcohol sulfates; sulfates of branched chain or secondary alcohols; alkyldimethyl-benzylammonium chlorides, salts of fatty acids or fatty acid mixtures; N-oxyalkylated fatty acid alkanolamides, and the like. Illustrative of specific surfactants there can be mentioned: sodium lauryl sulfate; polyoxyethylene lauryl ester; myristyl sulfate: glyceryl monostearate: triethanolamine oleate, sodium salt of palmitic methyl taurine; cetyl pyridinium chloride; lauryl sulfonate: myristyl sulfonate; lauric diethanolamide; polyoxyethylene stearate; ethoxylated oleoyl diethanolamide; polyethylene glycol amides of hydrogenated tallow; stearyldimethyl benzyl ammonium chloride; dodecylbenzene sodium sulfonate; 2-amino-2-methyl propanol; triethanolamine salt of p-dodecylbenzene sulfonate; triethanolamine salt of p-dodecylbenzene sulfonate; nonylnaphthalene sodium sulfonate; dioctyl sodium sulfosuccinate; sodium N-methyl-N-oleoyl taurate; oleic acid ester of sodium isothionate; sodium dodecyl sulfate and the sodium salt of 3-diethyl tridecanol-6-sulfate and the like. The quantity of surface active agent can vary over a wide range, such as from about 0.05% to 15% and preferably from about 0.10 to 5% by weight of the composition.

A thickening agent may also be incorporated in the dyeing composition of this invention which may be one or several of those commonly used in hair dyeing. These are exemplified by such products as sodium alginate or gum arabic, or cellulose derivatives, such as methylcellulose e.g.. Methocel 60 HG, or the sodium salt of carboxymethylcellulose, or hydroxyethylcellulose, e.g., Cellosize QP-40 or acrylic polymers, such as polyacrylic acid sodium salt, or inorganic thickeners, such as bentonite. The quantity of this thickening agent can also vary over a wide range, even as high as 20%. Ordinarily it will range from about 0.5 to 5% by weight of the composition. The viscosity of the composition may vary from about 1 cps to about 100,000 cps. For a typical lotion formulation, composition viscosity is from about 100 cps to about 10,000 cps.

It may also be useful to incorporate an antioxidant in the present dye compositions. A variety of antioxidants are known in the prior art which would be useful for this purpose. Among these mention may be made of the inorganic sulfites, e.g., sodium sulfite, thioglycollic acid and other mercaptans, butylated hydroxytoluene, sodium dithionite, various forms of ascorbic acid and their derivatives, e.g., sodium astorbate, erythorbic acid, ascorbyl palmitate, ascorbyl laurate, etc. The quantity of antioxidant used can vary appreciably. However, the concentration will, in general, be up to about 1%, typically 0.001 to 1% by weight.

The dyeing compositions of this invention are preferably aqueous compositions. The term aqueous composition is used herein in its usual generic sense as embracing any water-containing composition useful for the present purposes. This includes true solutions of the dye components aqueous medium, either alone or in conjunction with other materials, which are also dissolved or dispersed in the aqueous medium. The term aqueous composition also encompasses any mixture of the chlorite and the dye forming reactants with the aqueous medium either alone or together with other ingredients. The various components may be colloidally dispersed in the medium or may merely be intimately mixed therein. Moreover, the aqueous medium may comprise water or water and an additional or auxiliary solvent. Typical auxiliary solvents which may be used to enhance the solubility of the components include ethanol, carbitol, isopropanol, propylene glycol, ethylene glycol, diethylene glycol, diethylene glycol monoethyl ether, glycerine, etc.

The aqueous dyeing compositions of this invention can be prepared by conventional methods used in the hair dyeing art. Thus, they can be prepared by dissolving or suspending the components in the selected media with adequate mixing. Preparation may take place at ambient temperatures, i.e, 20° to 35° C., but solubility and rate of preparation can be enhanced utilizing elevated temperatures, for example 40° to 100° C.

The compounds employed in this invention are all known or can be prepared by known procedures.

By way of specific example but without limitation, there follows a description of various known routes for the preparation of derivatives of N-substituted-5,6-dihydroxyindoles which are useful in the present invention.

(1) Synthesis by cyclization of a dopamine derivative:

A suitable 3,4-dihydroxy-N-substituted phenethylamine material is converted by oxidative cyclization followed by chemical reduction to the N-substituted-dihydroxyindole as per the method for preparation of N-methyl-5,6-dihydroxyindoles from epinephrine described by G. L. Mattok and R. A. Heacock in the *Canadian Journal of Chemistry*, Volume 42, p. 284 (1964).

For example, N-isopropyl-3,4-dihydroxyphenethylamine (II) can be oxidized by an alkaline ferricyanide solution followed by reduction with ascorbic acid to give N-isopropyl-5,6-dihydroxyindole (III):

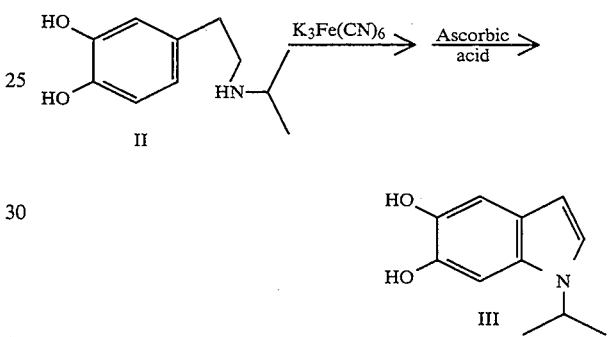

Similarly N-(4-aminobutyl)-5-6-dihydroxyindole (V) can be obtained from 3,4-dihydroxy-N-(4-nitrobutyl)-phenethylamine (IV):

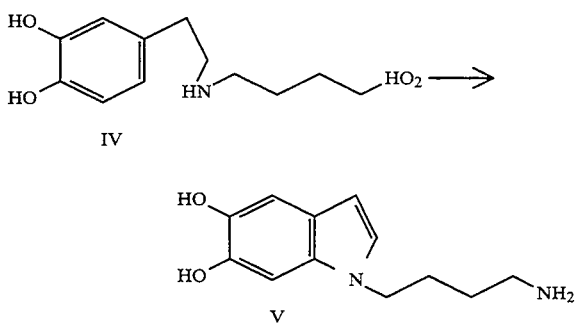

(b) Synthesis by condensation of a benzenoid compound and a nitrogen containing compound.

An alternative synthetic procedure is available by the methods described by A. Reissert in *Chemische Berichte*, Volume 30, page 1030 (1897) and C. D. Nenitzecu in *Bulletin of the Chemistry Society of Rumania*, Volume 11, page 37 (1929) where the indole is produced upon the condensation of a benzenoid radical with an appropriate N-containing material. For example, N-(2-hydroxyethyl)-5,6-dihydroxyindole (VI) can be obtained upon oxidative coupling of catechol (VII) with N-vinyl ethanolamine (VIII) followed by reduction.

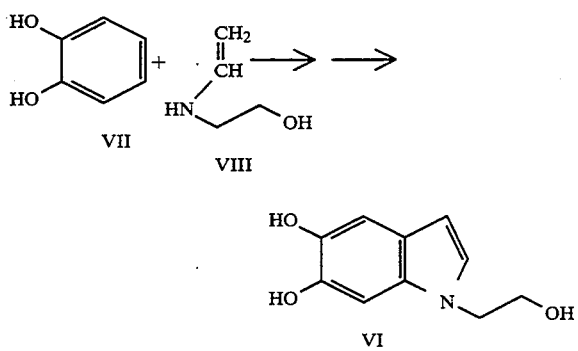

(c) Synthesis by addition of indole to an aryl compound is by the direct addition of the indole to an aryl or benzyl halide or azide to give the aryl or arylalkyl N-substituted-5,6-dihydroxyindole. Specifically, 5,6-diacetoxyindole (IX) is reacted with 2,4-dinitro-fluorobenzene (X) to give, after hydrolysis of the acetate radicals, N-(2,4-dinitropheny)-5,-6-dihydroxyindole (XI):

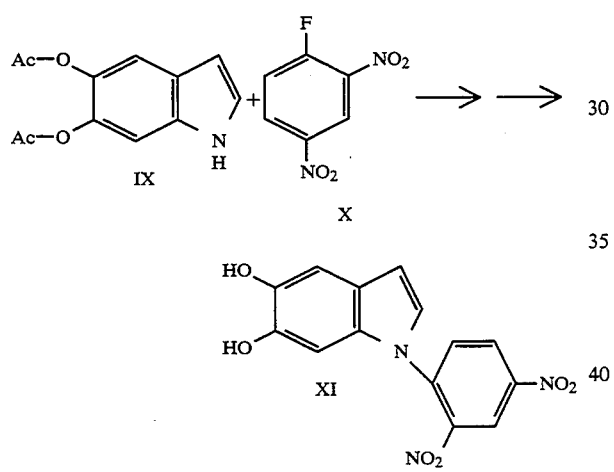

The following examples are illustrative of this invention and their use. They illustrate the advantages of the compositions of the invention.

The tristimulus values in the examples are standard Hunter chromacity values obtained by procedures well known to those skilled in the art. The values recorded manifest the ability of the compositions of the invention to be usefully employed in hair coloring processes.

In the Hunter Tristimulus System, L is a measure of lightness and darkness that is, the depth of the color of the hair tress. The lower the value of L the darker the color.

A decrease in the value of L indicates a darkening of the hair tress. In the case of bleached and blended gray hair, a lowering of the value of L shows deposition of hair dye on the tress.

The a value is a measure of the greenness or redness of the hair's color. As the a value increases, the hair has a more prominent red tonality. A lowering in the a value results in greener shades. The b value is a measure of the yellow and blue color. Higher b values indicate a more yellow hue in the hair.

EXAMPLE 1

DHI With Various Oxidizing Agents

A DHI composition was prepared containing 1.85 parts by weight of DHI, 0.2 parts by weight thioglycolic acid (TGA-an antioxidant) and 78 parts by weight of water adjusted to pH 6.5 with hydrochloric acid. This solution was employed as a standard solution to determine the efficacy of a number of oxidizing agents including those reported in U.S. Pat. No. 3,236,734.

For each test, approximately 16 ml of the DHI solution was combined with 4 g of an aqueous solution of the oxidant under test in the solutions defined in Table 2. The solution was applied to swatches of gray hair from the same source and left for 20 minutes. The treated hair was then rinsed, shampooed and dried. The dyeing conditions (concentrations, dyeing time, pH etc.) are chosen such that the experimental conditions of U.S. Pat. No. 3,236,734 are reproduced as closely as possible: The concentration of DHI is equivalent, on a molar basis to the concentration of the hydrochloride of 2,4-dihydroxy phenylamine (Example 19 of U.S. Pat. No. 3,236,734) and the concentration of the oxidants, sodium iodate, potassium persulfate, sodium perborate, is as described in this example. Sodium bromate and sodium chlorate (listed in the patent without specification of conditions) were used at equimolar concentration as sodium iodate.

Under these conditions, only sodium chlorite (Entry 9) and perborate (Entry 3) dye the hair to colors judged to be useful based on darkness and tonality. Perborate affords peroxide in aqueous solution. It is equivalent to aqueous peroxide itself—or to other peroxide sources, such as percarbonate, urea peroxide et cetera.

TABLE 2

| | Dyeing of Gray Hair[a] With Formula A (High DHI Concentration) | | | | |
|---|---|---|---|---|---|
| Entry | Oxidant, Added to 16cc DHI Solution | pH | L | a | b | Color |
| 1 | 0.4 g NaIO3, 0.4 g HOAc, 3.2 g H2O | 4.6 | 35.6 | 0.4 | 6.7 | Gray |
| 2 | 0.8 g K2S2O8, 0.4 g HOAC, 2.8 G H2O | 2.4 | 34.2 | 0.8 | 7.2 | Gray |
| 3 | 0.3 g NaBO3, 0.4 g Na2CO3, 3.3 g H2O | 9.2 | 22.8 | 0.9 | 2.3 | Dk. Gray |
| 4 | 0.4 g NaBrO3, 0.4 g HOAc, 3.2 g H2O | 4.4 | 27.3 | −0.2 | 4.4 | Gray |
| 5 | 0.4 g NaClO3, 0.4 g HOAc, 3.2 g H2O | 4.5 | 34.4 | 0.6 | 6.5 | Gray |
| 6 | 4 g aq. NaOCl (4–6%) | 5.7 | 30.7 | 0.2 | 4.8 | Gray |
| 7 | 4 g 6% H2PO2 | 6.0 | 27.9 | 0.5 | 4.4 | Gray |
| 8 | 4 g 6% H2O2, 0.4 g urea | 6.0 | 27.0 | 0.5 | 4.2 | Gray |
| 9 | 0.2 g NaClO2, 0.4 g HOAc, 3.4 g H2O | 4.4 | 18.7 | 0.6 | 1.6 | Dk. Gray/Blk |

[a]Undyed hair: L 35.8 a 0.2, b 6.6

Similar results are obtained with N-methyl- and N-ethyl-5,6,dihydroxyindole and with the corresponding 2-methyl- and 2-ethyl-compounds.

EXAMPLE 2

Comparison of Sodium Chlorite (Entry III) With Other Oxidants

This example was conducted to show the unexpected superiority of sodium chlorite as an oxidant compared with hydrogen peroxide or other sources of peroxide, such as perborate.

Formulations were prepared, which contained DHI at a lower concentration than in Example 1 (DHI concentration 0.5% after mixing with oxidant). This would be a preferred concentration for a commercial product, since DHI is an expensive raw material. The formulations contain different alkaline agents to adjust the pH to the desired value. This is summarized in Table 3.

Entries 1–5 demonstrate, that, in contrast to sodium chlorite, peroxide, or its substantial equivalent perborate are only efficient as oxidants at alkaline pH.

Entries 8, 9 and 10 show, that the efficacy of peroxide is further increased, when ammonia is used as the alkalizing agent.

Entry 11 illustrates the use of sodium chlorite. The data demonstrate, that with peroxide as oxidant, the efficacy of sodium chlorite can be approached (but still not matched) only at high pH and high ammonia concentrations both of which are unacceptable because of the strong odor of ammonia and the likelihood of hair damage at the high pH. Only sodium chlorite imparts a deep brown color at low pH, without ammonia, from solutions containing relatively low concentrations of DHI.

TABLE 3

Dyeing of Gray Hair With Low Concentration of DHI 0.5%

| Entry | Oxidant | (%) | Base | (%) | pH | Hunter L | Trist. a | val. b | color |
|---|---|---|---|---|---|---|---|---|---|
| 1 | $H_2O_2$ | (0.5) | MEA | (1.8) | 9.9 | 27.6 | 0.2 | 2.9 | dark gray |
| 2 | $H_2O_2$ | (0.5) | MEA | | 8.0 | 32.7 | 0.2 | 6.2 | gray |
| 3 | $H_2O_2$ | (0.5) | MEA | | 7.0 | 32.4 | 0.4 | 5.9 | gray |
| 4 | $NaBO_3$ | (1.5) | MEA | | 9.9 | 28.3 | 0.2 | 3.0 | dark gray |
| 5 | $NaBO_3$ | (1.5) | MEA | | 8.0 | 32.8 | 0.4 | 6.1 | gray |
| 6 | $NABO_3$ | (1.5) | $Et_2NH$ | (1.6) | 10.5 | 27.8 | 0.3 | 3.3 | gray |
| 7 | $NaBO_3$ | (3.0) | $Et_2NH$ | (1.6) | 10.5 | 27.3 | 0.4 | 3.4 | gray |
| 8 | $NaBO_3$ | (1.5) | $NH_3$ | (0.5) | 9.8 | 25.4 | 0.6 | 2.8 | dark gray |
| 9 | $NaBO_3$ | (3.0) | $NH_3$ | (0.5) | 9.8 | 25.0 | 0.5 | 3.0 | dark |
| 10 | $NaBO_3$ | (1.5) | $NH_3$ | (1.3) | 10.8 | 21.7 | 0.8 | 2.0 | dark gray |
| 11 | $NaClO_2$ | (3.6) | | | 7.0 | 21.9 | 1.5 | 3.9 | dark brown |

Similar results are obtained with N-isopropyl-5,6-dihydroxyindole and with N-(2,4-dinitrophenyl)-5,6-dihydroxyindole.

EXAMPLE 3

Additional Comparisons of Sodium Chlorite

This example was conducted to compare the efficacy of sodium chlorite with oxidizing agents specifically mentioned in U.S. Pat. No. 3,194,734.

The following compositions were prepared: (as described in U.S. Pat. No. 3,194,734)

| FORMULA B | | FORMULA C | | FORMULA D | |
|---|---|---|---|---|---|
| DAI | 1 | DAI | 1 | DAI | 1 |
| Nonyl-Nonoxynol-49 | 9 | Nonyl-Nonoxynol-49 | 9 | Nonyl-Nonoxynol-49 | 9 |
| MEA | 2 | Ammonia (20%) | 3 | Urea | 7.5 |
| TGA (50%) | 0.1 | TGA (50%) | 0.1 | Diethylamine | 2 |
| Water | 87.9 | Water | 86.9 | TGA (50%) | 0.1 |
| | | | | Water | 80.4 |

All components were dissolved in water with heating to about 50°–60° C., until complete dissolution of the various ingredients. This temperature increase brings about the deacetylation of DAI and therefore the formation of 5,6-dihydroxyindole (DHI). 1 g DAI results in approximately 0.64 g DHI.

The ingredients and methods of preparation of the formulations are identical to what has been described in U.S. Pat. No. 3,194,734 (examples 1, 2 and 3) with one exception: Nonyl-Nonoxynol 49 was used instead of "Cemulsol 132", due to the unavailability of this component. Cemulsol 132 is a non-ionogen condensation product of ethylene oxide and a naphthol compound. Nonyl-Nonoxynol 49 is a non-ionogen condensation product of ethylene oxide and a benzene compound. This substitution has no effect on the described dyeing results.

In each entry the oxidant was added immediately before use to the formulation (ambient temperature), applied to hair and left for minutes. The hair was rinsed with water, shampooed and dried. Hunter Tristimulus values were measured.

The results are shown in Table 4.

TABLE 4

Dyeing of Gray Hair With Formulas B, C and D
(Low DHI Concentration)

| Entry | Dye Solution | $pH^a$ | L | a | b | Color |
|---|---|---|---|---|---|---|
| 1 | 10 cc formula C, 1 cc 6% $H_2O_2$ | 10.0 | 22.5 | 1.2 | 1.0 | Dk. Gray |
| 2 | 10 cc formula D, 0.2 g $(NH_4)_2S_2O_8$ | 9.2 | 31.9 | 0.6 | 4.7 | Gray |
| 3 | 10 cc formula C, 0.02 g $CoCl_2$ | 9.9 | 27.6 | 0.0 | 2.7 | Gray |
| 4 | 10 cc formula C, 0.02 g Mn-lact. | 9.2 | 29.4 | −0.3 | 3.4 | Bluish Gray |
| 5 | 10 cc formula B, 1 cc 6% $H_2O_2$ | 9.9 | 26.8 | 0.2 | 2.8 | Gray |
| 6 | 10 cc formula B, 0.4 g $NaClO_2$ in 1 g $H_2O$ | 7.0 | 21.9 | 1.5 | 3.9 | Brown |

$^a$After addition of oxidant.

With $H_2O_2$ (Table 4, Entry 1), the darkness of the hair is comparable to sodium chlorite (Table 3, Entry 6). However, the tonality is different.

To obtain a dark dyeing as in Table 4, Entry 1 (with rel. low DHI concentration and $H_2O_2$ as oxidant) the presence of a substantial amount of ammonia is required. Without ammonia at equal DHI-concentration, the dyeing is weaker (see Table 4, Entry 5).

Tonality: An example of Hunter Tristimulus values of natural dark and medium brown hair is the following:

|  | L | a | b |
|---|---|---|---|
| dark brown | 16.0 | 1.8 | 2.6 |
| med. brown | 23.6 | 3.0 | 6.9 |

It is apparent that at a darkness level of L at about 22, the b-value should be more than twice the amount of the a-value. This is achieved with hair dyed with DHI/sodium chlorite (Table 4, Entry 6), but not with hair dyed with DHI/$H_2O_2$ at the conditions of Entry 1, Table 4. Only the DHI/sodium chlorite dyed hair appears natural brown.

EXAMPLE 4

Compositions Containing Primary Intermediate and Coupler

An aqueous solution, containing 0.3% DHI, 0.4% p-aminophenol, 0.4% 5-amino-o-cresol in a pH 7 phosphate buffer was prepared (solution 1). 3 ml of an aqueous solution of sodium chlorite (4%) was added to 5 ml of solution 1; the mixture was applied to (gray) hair and left for 15 minutes. The hair was rinsed with water, shampooed and dried. The hair had a medium brown color with Hunter Tristimulus values L 21.8 a 1.9 b 5.1. If sodium chlorite was omitted in an otherwise identical dyeing solution, the hair was dyed to a light brown color having the Hunter Tristimulus values L 28.5 a 1.3 b 6.9. If DHI was omitted in an otherwise identical dyeing solution (with sodium chlorite), the hair was dyed to a light brown color with Hunter Tristimulus values L 27.9 a 2.1 b 7.4.

Similar results are obtained with N-methyl- and N-ethyl-5,6,dihydroxyindole and with the corresponding 2-methyl- and 2-ethyl-compounds.

What is claimed is:

1. A dye composition comprising an aqueous solution containing from about 0.1% to 5% by weight of sodium chlorite together with from about 0.1% to 3% by weight of a compound selected from the group consisting of 5,6-dihydroxyindoline and an indole which is a melanin precursor represented by the formula:

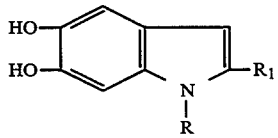

wherein R is hydrogen, alkyl, hydroxyalkyl or aminoalkyl, the alkyl group containing up to eight carbon atoms, aryl, or substituted aryl containing up three reaction inert substituents, $R_1$ is hydrogen or alkyl containing up to six carbon atoms and mixtures of said compounds, said composition having a pH effective for dyeing hair without causing oxidative damage to the hair.

2. A dye composition of claim 1 wherein the melanin precursor is 5,6-dihydroxyindole.

3. A hair dye composition of claim 1 further comprising at least one of the following: surface active agent in an amount up to about 5% by weight, thickening agent in an mount up to about 20% by weight and antioxidant in an amount up to about 1% by weight, said composition having a pH from about 7 to about 9.

4. An oxidative dye composition of claim 1, 2 or 3 additionally containing sufficient amounts of an oxidative primary intermediate and coupler to react and form a tinctorially effective amount of a hair dye.

5. An oxidative dye composition of claim 4 wherein the amounts of oxidative primary intermediate and coupler are each from about 0.01 to about 2% by weight.

6. An oxidative dye composition of claim 1, 2 or 3 additionally containing from about 0.1 to 1% by weight of 5,6-dihydroxyindole-2-carboxylic acid or a lower alkyl ester thereof.

7. A package containing two separate compositions, the first comprising an aqueous solution containing sodium chlorite, the second containing a dye composition comprising an aqueous solution containing a compound selected from the group consisting of 5,6-dihydroxyindoline and an indole which is a melanin precursor represented by the formula:

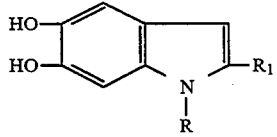

wherein R is hydrogen, alkyl, hydroxyalkyl or aminoalkyl, the alkyl group containing up to eight carbon atoms, aryl, or substituted aryl containing up to three reaction inert substituents, $R_1$ is hydrogen or alkyl containing up to six carbon atoms and mixtures of said compounds; the amount of sodium chlorite in the first composition being sufficient so that when the two compositions are mixed, the amount of sodium chlorite salt in the resulting composition will be from about 0.1% to 5% by weight; the amount of melanin precursor in the second composition being sufficient so that when the two compositions are mixed, the resulting composition will contain from about 0.1% to 3% by weight of melanin precursor, the resulting composition having a pH effective for dyeing hair without causing oxidative damage to hair.

8. A package of claim 7 wherein the melanin precursor is 5,6-dihydroxyindole.

9. A package of claim 7, the first two compositions further comprising at least one of the following in an amount such that the resulting composition will contain: surface active agent in an amount up to about 15% by weight, thickening agent in an amount up to about 20% by weight and anti-oxidant in an amount up to about 1% by weight, said resulting composition having a pH from about 7 to about 9.

10. A package of claims 7, 8 or 9 additionally containing sufficient amounts of an oxidative primary intermediate and coupler to react and form a tinctorially effective amount of a hair dye.

11. A package of claim 10 wherein the amounts of oxidative primary intermediate and coupler are each from about 0.01% to about 2% by weight.

12. A package of claims 7, 8 or 9 additionally containing from about 0.1 to 1% by weight of 5,6-dihydroxyindole-2-carboxylic acid or a lower alkyl ester thereof.

13. A method of dyeing hair comprising applying to the hair an oxidative composition of claim 1, 2 or 3.

* * * * *